United States Patent [19]

LaMattina

[11] Patent Number: 4,673,677
[45] Date of Patent: Jun. 16, 1987

[54] METHOD FOR TREATMENT OF GASTROINTESTINAL DISORDERS

[75] Inventor: John L. LaMattina, Ledyard, Conn.
[73] Assignee: Pfizer Inc., New York, N.Y.
[21] Appl. No.: 764,351
[22] Filed: Aug. 9, 1985

Related U.S. Application Data

[62] Division of Ser. No. 538,233, Oct. 3, 1983, Pat. No. 4,554,276.

[51] Int. Cl.$^4$ .................. A61K 31/505; C07D 239/47
[52] U.S. Cl. .................. 514/272; 514/273; 514/926; 514/927; 544/298
[58] Field of Search ............... 544/298; 514/272, 273, 514/927, 926

[56] References Cited

U.S. PATENT DOCUMENTS 4,374,136 2/1983 Hill et al. ........................ 544/298
4,416,885 11/1983 Huvé ............................. 514/272
4,435,396 3/1984 LaMattina et al. ................ 514/927

FOREIGN PATENT DOCUMENTS 2045756 11/1980 United Kingdom .

OTHER PUBLICATIONS

Asadov, D. A., *Chemical Abstracts*, 70:2232w, (1969).
Esanu, Andre, *Chemical Abstracts*, 94:103410d, (1981).

*Primary Examiner*—Donald G. Daus
*Assistant Examiner*—Stephen M. Kapner
*Attorney, Agent, or Firm*—Charles J. Knuth; Peter C. Richardson; Mark Dryer

[57] ABSTRACT

A method for the treatment of gastrointestinal disorders in a patient which comprises administering to the patient a gastric anti-secretory effective amount of a 2-amino-5-hydroxy-4-methylpyrimidine or a substituted amino derivative thereof, optionally in admixture with an additional gastric anti-secretory agent.

3 Claims, No Drawings

METHOD FOR TREATMENT OF GASTROINTESTINAL DISORDERS

This is a division of application Ser. No. 538,233, filed on Oct. 3, 1983, now U.S. Pat. No. 4,554,276.

BACKGROUND OF THE INVENTION

This invention relates to novel hydroxy-pyrimidine derivatives, more particularly to 2-amino and substituted amino-5-hydroxy-4-methylpyrimidines. This invention is also concerned with a process for the preparation of such novel compounds and with pharmaceutical compositions containing the novel compounds as active ingredients.

United Kingdom Patent Application No. 2045756, published Nov. 5, 1980, discloses 2-isopropylamino-5-hydroxy-pyrimidine as an agent for the treatment of muscular dystrophy. There is no disclosure in this prior application of any 4-methyl analogs.

Chronic gastric and duodenal ulcers, together known as peptic ulcers, are the subject of a variety of treatments, including special diets, drug therapy and surgery, depending upon the severity of the condition. Particularly valuable therapeutic agents useful for the treatment of gastric hyperacidity and peptic ulcers are the histamine-$H_2$ receptor antagonists, which block the action of the physiologically-active compound histamine at the $H_2$-receptor sites in the animal body and thereby inhibit the secretion of gastric acid.

Copending Patent Application Ser. No. 376486 discloses certain 2-guanidino-4-(2-substituted amino-4-imidazolyl)thiazole derivatives as cytoprotective $H_2$-antagonists which inhibit ethanol-induced ulcers in rats and thereby have clinical value in the inhibition of gastric ulcers. The cytoprotective $H_2$-antagonists or application No. 376486 are prepared from intermediate 2-amino-5-acetylimidazoles and these key intermediates are prepared from 2-amino-5-acetyl oxazole by a rearrangement reaction which is disclosed in application No. 376486.

The 5-hydroxypyrimidine derivatives of the present invention, which are not described per se in application No. 376486, are minor products of the aforesaid rearrangement reaction and the preparation thereof is described in more detail hereinafter.

It has now been found that the novel 5-hydroxypyrimidine derivatives produced as by-products in the general reaction disclosed in application No. 376486, but not isolated or described per se in the disclosure of that application, are valuable therapeutic agents.

SUMMARY OF THE INVENTION

Thus, in accordance with the present invention there is provided a pharmacologically-active substituted pyrimidine derivative having the general formula:

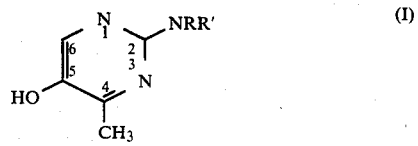

wherein R is hydrogen or $(C_1-C_{15})$alkyl and R' is hydrogen, $(C_1-C_{15})$alkyl, $(C_5-C_8)$cycloalkyl, $(C_3-C_{15})$alkenyl, phenyl, $(C_4-C_5)$heteroaryl, $(C_5-C_{17})$heteroaralkyl, $(C_7-C_{20})$aralkyl or substituted aralkyl wherein the substitutent is halo, $(C_1-C_3)$alkyl, $(C_1-C_3)$alkoxy or trifluoromethyl; or R and R' together with the nitrogen atom to which they are attached form a piperidyl group, a substituted piperidyl group wherein the substituent is $(C_1-C_{15})$alkyl or $(C_7-C_{20})$aralkyl, or a pyrrolidinyl group, or a pharmaceutically-acceptable acid addition salt thereof.

The novel compounds of the invention are inhibitors of leukotriene synthesis and potent inhibitors of 5-lipoxygenase enzyme (5-LO) in vitro which makes them valuable agents in the treatment of asthma, inflammation, cardiovascular spasm, psoriasis and cancer. Furthermore the compounds are "cytoprotective", i.e. they inhibit ethanol-induced ulcer formation in rats and thus they are of interest as non-antisecretory anti-ulcer agents.

Preferred compounds of the invention are 2-amino-5-hydroxy-4-methylpyrimidine derivatives of formula (I) wherein R is hydrogen or methyl and R' is hydrogen, $(C_1-C_{10})$alkyl, cyclopentyl, cyclohexyl, $(C_3-C_8)$alkenyl, phenyl, furyl, thienyl, $(C_7-C_{12})$phenylalkyl or substituted phenylalkyl wherein the substituent is chloro, $(C_1-C_3)$alkyl, methoxy or trifluoromethyl; or R and R' together with the nitrogen atom to which they are attached form a piperidyl group, a substituted piperidyl group wherein the substituent is $(C_7-C_{12})$phenylalkyl, or a pyrrolidinyl group, or a pharmaceutically-acceptable acid addition salt thereof.

More preferred compounds are those of formula (I) wherein R is hydrogen or methyl and $R^1$ is $(C_6-C_{10})$alkyl, cyclopentyl, cyclohexyl, $(C_6-C_8)$ alkenyl, phenyl, $(C_7-C_{12})$ phenylalkyl or substituted phenylalkyl wherein the substituent is chloro, $(C_1-C_3)$alkyl, methoxy or trifluoromethyl; or R and R' together with the nitrogen atom to which they are attached form a piperidyl group, a substituted piperidyl group wherein the substituent is $(C_7-C_{12})$phenylalkyl, or a pyrrolidinyl group, or a pharmaceutically-acceptable acid addition salt thereof.

Particularly preferred compounds are the following:

The compound of formula (I) wherein R is hydrogen and R' is $(CH_2)_6C_6H_5$, i.e. 2-[N-(6-phenylhexylamino)]-5-hydroxy-4-methylpyrimidine, or the hydrochloride salt thereof;

The compound of formula (I) wherein R is hydrogen and R' is $(CH_2)_4C_6H_5$, i.e. 2-[N-(4-phenylbutylamino)]-5-hydroxy-4-methylpyrimidine, or the hydrochloride salt thereof; and The compound of formula (I) wherein R and R' together with the nitrogen atom to which they are attached form the group of the formula:

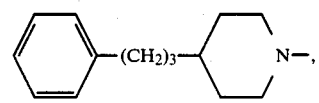

i.e. 2-[4-(3-phenylpropyl)-N-piperidino]-5-hydroxy-4-methylpyrimidine or the hydrochloride salt thereof.

The present invention also provides a novel process for the preparation of a compound having the general formula:

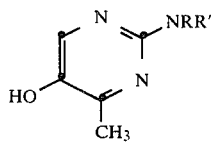 (I)

wherein R is hydrogen or $(C_1-C_{15})$alkyl and R' is hydrogen, $(C_1-C_{15})$alkyl, $(C_5-C_8)$cycloalkyl, $(C_3-C_{15})$alkenyl, phenyl, $(C_4-C_5)$heteroaryl, $(C_5-C_{17})$heteroaralkyl, $(C_7-C_{20})$aralkyl or substituted aralkyl wherein the substituent is halo, $(C_1-C_3)$alkyl, $(C_1-C_3)$alkoxy or trifluoromethyl; or R and R' together with the nitrogen atom to which they are attached form a piperidyl group, a substituted piperidyl group wherein the substituent is $(C_1-C_{15})$alkyl or $(C_7-C_{20})$aralkyl, or a pyrrolidinyl group, or an acid addition salt thereof in substantially pure form; which comprises reacting 5-acetyl-2-aminooxazole of the formula:

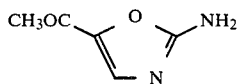 (II)

with an amine of the formula RR'NH in the presence of water at a temperature within the range of 90° to 125° C., and isolating the desired compound of formula (I) from the resulting product mixture, and, if desired, converting the compound into a pharmaceutically-acceptable acid addition salt by reaction with an appropriate acid.

The 5-acetyl-2-aminooxazole of formula (II) above is a known compound. Kochetikov et al., Chemical Abstracts 54: 14230h (1960). A preferred method for the preparation thereof is disclosed in application No. 376486 and is repeated hereinafter.

The amines used in the preparation of the compounds according to the invention are generally commercially available or may be prepared by standard methods. A specific method for the preparation of 6-phenylhexylamine which is the starting amine for a particularly preferred compound of the invention is particularly described hereinafter.

DETAILED DESCRIPTION OF THE INVENTION

The preparation of the compounds of formula (I) may be illustrated by the following reaction scheme:

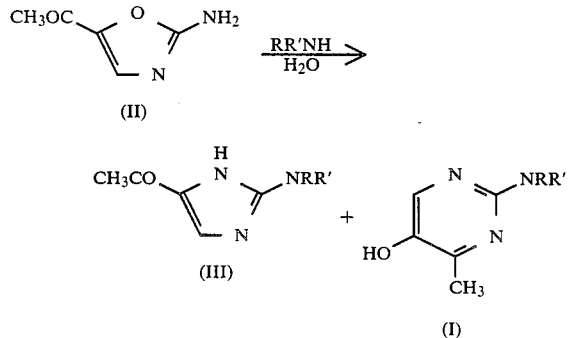

The general procedure for carrying out the above process comprises heating a mixture of 5-acetyl-2-aminooxazole (formula II); 3-6 equivalents of the appropriate amine of formula RR'NH and water at a temperature of 90° to 125° C. (external) until all the oxazole is consumed, as monitored by t.l.c. (2–96 hours). The mixture is then concentrated, distilled if necessary to remove the excess amine, and the residue chromatographed over silica gel using 4:1 ethyl acetate/hexane as eluent. The desired pyrimidine of formula (I) is eluted first and recrystallized from an appropriate solvent. The preferred solvent for specific compounds according to the invention is given in the Examples.

If desired, the imidazole of formula (III) then may be eluted from the column using 19:1 chloroform/methanol as eluent. As stated above, the 2-amino-5-acetylimidazole of formula (III) is a key intermediate in the preparation of the cytoprotective thiazole derivatives disclosed in application No. 376486.

Where the pyrimidine product of formula (I) is an oil it is converted to the hydrochloride salt by dissolving in alcohol, adding hydrochloric acid gas to saturation, evaporating the alcohol followed by trituration of the residue with ether.

The novel compounds of formula (I) are useful as inhibitors of lipoxygenase synthesis and as cytoprotective agents for the treatment of various pulmonary, gastrointestinal, inflammatory, dermatological and cardiovascular conditions, as well as cancer. In particular, the compounds have utility, both as the sole active agent and also in combination with other active agents, for the treatment of asthma, bronchitis, peptic ulcers, psoriasis, arthritis, inflammatory bowel disease or cardiovascular spasm, such as acute myocardial infarctions.

Accordingly the present invention further provides a pharmaceutical composition comprising a pharmaceutically-effective amount of a compound of formula (I) or a pharmaceutically-acceptable acid addition salt thereof in admixture with a pharmaceutically-acceptable diluent or carrier.

The pharmaceutical composition according to the invention may also include a standard non-steroidal anti-inflammatory agent or an additional gastric antisecretory agent.

It has been found that the use of the compounds of this invention together with the aforesaid active agents is particularly beneficial. Without wishing to be bound by any theory, it would appear that the beneficial effect produced by the co-administration of the compounds of the invention with other active agents as herein defined arises either from a synergistic or additive action of the two active agents or from the fact that the compounds of this invention have a tendency to suppress deleterious side-effects which may arise when the other agents are used alone, such as the gastric irritation caused by non-steroidal anti-inflammatory agents.

The invention still further provides a method for the treatment of asthma, bronchitis, peptic ulcers, psoriasis, arthritis, inflammatory bowel disease or acute myocardial infarctions in a patient, which comprises administering to the patient a pharmaceutically-effective amount of a compound of formula (I) or a pharmaceutically-acceptable acid addition salt thereof.

In accordance with the preferred embodiments described above, the invention yet further provides a method for the treatment of arthritis and inflammation conditions in a patient, which comprises co-admistering to the patient a pharmaceutically-effective amount of a compound of formula (I) or a pharmaceutically-acceptable acid addition salt thereof and a standard non-steroidal anti-inflammatory agent.

The invention also provides a method for the treatment of peptic ulcers and other gastrointestinal disorders in a patient, which comprises co-administering to the patient a pharmaceutically-effective amount of a compound of formula (I) or a pharmaceutically-acceptable acid addition salt thereof and an additional gastric anti-secretory agent.

Preferred anti-inflammatory agents used in the above embodiments of the invention are:
aspirin;
1-(p-chorobenzoyl)-5-methoxy-2-methylindole-3-acetic acid, known as indomethacin and described in U.S. Pat. No. 3,161,654, now expired;
(+)-6-methoxy-α-methyl-2-naphthaleneacetic acid, known as naproxen and described in U.S. Pat. No. 3,641,161;
2-[(2,6-dichlorophenyl)amino]-benzene acetic acid, monosodium salt, known as diclofenac;
α-methyl-4-(2-methylpropyl)-benzene acetic acid, known as ibuprofen and described in U.S. Pat. No. 3,385,886; and
4-hydroxy-2-methyl-N-2-pyridyl-2H-1,2-benzothiazine-3-carboxamide 1,1-dioxide, known as piroxicam and described in U.S. Pat. No. 3,591,584.

Preferred gastric anti-secretory agents which may be co-administered with the compounds of this invention include:
2-cyano-1-methyl-3-[2-{[(5-methylimidazol-4-yl) methyl]thio}ethyl]guanidine, known as cimetidine and described in U.S. Pat. No. 3,950,333;
N-[2-{[5-[(dimethylamino)methyl]furfuryl]thio} ethyl]-N'-methyl-2-nitro-1,1-ethenediamine, known as ranitidine;
3-[[[2-(diaminomethylene)amino]-4-thiazolyl]methylthio]-N-2-sulfamoylpropionamidine, known as famotidine;
2-cyano-1-[2-[[(5-methylimidazol-4-yl)methyl]thio]-ethyl]-3-(2-propynyl)guanidine monohydrochloride, known as etintidine;
5-amino-1-methyl-1H-1,2,4-triazol-5-yl[3-(α-piperidino-m-tolyloxy)-propyl]amine, known as lamtidine; and
2-guanidino-4-(2-methyl-4-imidazolyl) thiazole and the hydrohalide salts thereof, particularly the hydrobromide, as described in U.S. Pat. No. 4,374,843.

For treatment of the various conditions described above the compounds of the invention may be administered to a subject in need of treatment, either alone or in combination with the other described active agents, by a variety of conventional routes of administration, including oral, parenteral and topical.

In general, a therapeutically-effective dose for the active compounds of the invention will range from 1 to 100 mg/kg. body weight of the subject to be treated per day, with a preferred dose of 1 to 20/mg/kg. per day.

When used in combination with other active agents, as described above, the active compound of the invention will be co-administered with a therapeutically-effective dose of the other active agent. For example, in the treatment of inflammation a therapeutically-effective daily dose of a compound of the invention would be co-administered with 20 mg. of piroxicam.

As another example, for the treatment of peptic ulcers, a therapeutically-effective dose of a compound of the invention would be co-administered with 300 mg. of cimetidine four times a day.

Variations in dosage will necessarily occur depending upon the condition of the subject and the physician responsible for administration will determine the appropriate dose for the individual subject.

The following Preparations illustrate the preparation of starting compounds used in the preparation of the compounds according to the invention. The subsequent Examples illustrate the preparation of compounds of formula (I) according to the process of the invention.

PREPARATION A

Preparation of 5-Acetyl-2-Aminooxazole (Formula (II))

A mixture of 132.3 g (0.80 mole) of 2-bromo-1-hydroxy-3-oxo-1-butene, 120.1 g (2.0 mole) of urea, and 1.85 l of acetone was heated at reflux with overhead stirring for one hour. The mixture was concentrated and the oil residue was taken up into 600 ml of water, then made basic with concentrated ammonium hydroxide. After sitting at room temperature for 0.5 hour, a precipitate formed. This was collected, and dried in vacuo to give 61.1 g of crude product. The filtrate was again concentrated and the oil residue taken up in 50 ml of water and again made basic with concentrated ammonium hydroxide. After sitting overnight a second crop of crude product, amounting to 17.6 g was isolated. Both crops were combined and recrystallized from methanol to give 50.3 g (50%) of 5-acetyl-2-amino-oxazole, m.p. 214°–215° C.

PREPARATION B

Preparation of 6-Phenylhexylamine a. 6-Phenylcapronitrile. A solution of 50.0 g (0.284 mole) of 6-bromocapronitrile in 550 ml of benzene was cooled to 5° C. and to this was added 77.3 g (0.580 mole) of anhydrous aluminum chloride in portions over a 10 minute period. The ice bath was removed and the vigorously stirred mixture was warmed slowly to reflux. After 2 hours at reflux, the mixture was cooled to room temperature, then poured slowly into a mixture of 50 ml of concentrated hydrochloric acid and 250 ml of ice water. The layers were separated and the aqueous portion was extracted twice with 125 ml portions of ether. The combined organic extracts were washed with 100 ml of saturated sodium bicarbonate solution, 100 ml of saturated sodium chloride solution, then dried over sodium sulfate, filtered, and evaporated leaving 53 g of a crude red/brown oil. Distillation under reduced pressure afforded 42.4 g (86%) of the nitrile as a pale yellow oil, bp 136°–140° C./2.5 mm of Hg.

b. 6-Phenylhexylamine. A mixture of 42.4 g (0.245 mole) of 6-phenylcapronitrile, 3 g of Raney nickel, 200 ml of ethanol, and 30 ml of concentrated ammonium hydroxide was hydrogenated at 43 psi, and room temperature for 24 hours. The catalyst was removed by filtration and the filtrate concentrated leaving an oil. Distillation under reduced pressure afforded 32.8 g (75.6%) of 6-phenylhexylamine as a colorless oil, bp 118°–123° C./1.5 mm of Hg. NMR (CDCl$_3$): 7.20 (s, 5H); 2.80–2.55 (m, 4H); 1.80–1.10 (m, 8H); 1.00 (s, 2H - exchangeable with D$_2$O).

Analogous phenyl alkylamines may prepared in a similar manner to that illustrated in Preparation B using the appropriate starting nitriles.

PREPARATION C

Preparation of 6-(p-chlorophenyl)hexylamine.

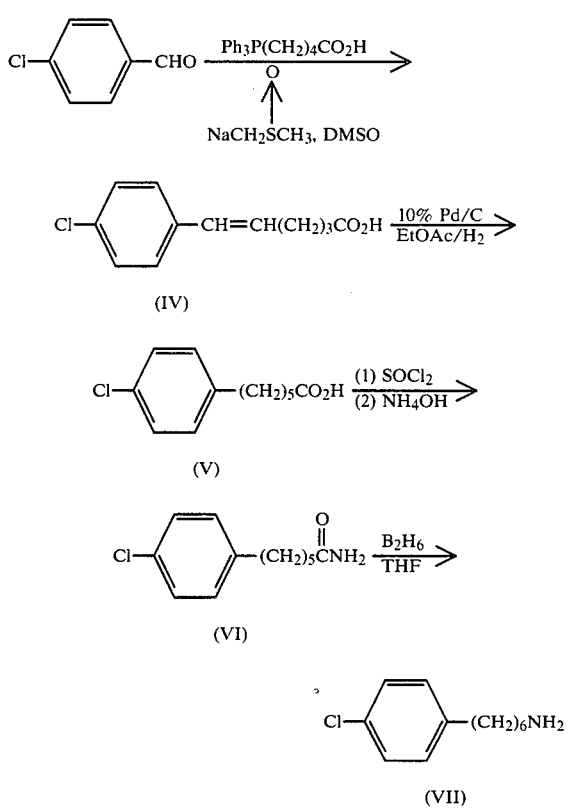

6-(p-Chlorophenyl)hex-5-enoic acid (IV).

A solution of sodium dimsylate (prepared from 12.5 g of 50% sodium hydride and dry DMSO) was stirred at 30°–35° C. and 39.1 g (0.088 mole) of 5-triphenylphosphonium pentanoic acid bromide was added in portions. The resulting dark red solution was stirred at room temperature for 10 minutes, then a solution of 10.0 g (0.068 mole) of p-chlorobenzaldehyde in 20 ml of dry DMSO was added dropwise over 10 minutes (cooling was necessary to maintain 30°–35° C. temperature). The mixture was stirred at room temperature for 18 hours, then poured into 300 ml of water and acidified to pH 2 with 6N hydrochloric acid. The mixture was extracted twice with 500 ml portions of ethyl acetate. The combined ethyl acetate portions were extracted three times with 35 ml portions of sodium hydroxide. The combined sodium hydroxide extracts were brought to pH 3 with 6N hydrochloric acid, then reextracted with ethyl acetate. The combined ethyl acetate extracts were dried over magnesium sulfate, filtered, and evaporated leaving a semi-solid that was chromatographed over silica gel using 19:1 methylene chloride/methanol as eluent. The product, isolated in quantitative yield was contaminated with triphenyl-phosphine oxide, but was of sufficient purity to utilize in the next step.

6-(pChlorophenyl)hexanoic acid (V).

A mixture of 49.3 g (0.219 mole) of 6-(p-chlorophenyl)hex-5-enoic acid, 3.0 g of 10% Pd/C, and 300 ml of ethyl acetate was hydrogenated at 45 psi and room temperature for 20 hours. The catalyst was removed by filtration through a Celite pad, and the filtrate concentrated to give 21.3 g (43%) of V as an oil, which was used without further purification.

6-(p-Chlorophenyl)hexanamide (VI).

A mixture of 21.3 g (0.094 mole) of 6-(p-chlorophenyl)hexanoic acid (V) and 95 ml of thionyl chloride was heated at reflux for 3 hours. The mixture was cooled, then concentrated. The residue was dissolved in 45 ml of ether and this solution was slowly added to 67 ml of concentrated ammonium hydroxide at 5° C. After addition, the mixture was vigorously stirred at 5° C. for one hour, then diluted with 100 ml of water and extracted with ether. The combined ether extracts were dried (magnesium sulfate) filtered, and evaporated leaving 16.4 g (77%) of VI as a tan solid mp. 87°–89° C.

6-(p-Chlorophenyl)hexylamine (VII).

A solution of 16.4 g (0.073 mole) of 6-(p-chlorophenyl hexanamide (VI) in 30 ml. of dry tetrahydrofuran was added dropwise to a stirred solution of 170 ml of 1.0M diborane/tetrahydrofuran solution (Aldrich) at 0° C. under a nitrogen atmosphere. After addition, the mixture was stirred at 0° C. for 15 minutes, then warmed to reflux and kept there for 2.5 hours. The mixture was cooled to room temperature, and 85 ml of 6N hydrochloric acid was added cautiously to quench the reaction. The solvent was removed and the aqueous mixture was brought to pH 10 with 10% sodium hydroxide solution. The aqueous mixture was extracted three times with 60 ml portions of ethyl acetate. The combined ethyl acetate extracts were washed with saturated sodium chloride solution, dried over sodium sulfate, filtered, and evaporated leaving an oil. Distillation under reduced pressure afforded 10.4 g (67%) of VII as a colorless oil, bp. 108°–115° C. (0.3 torr).

Analogous substituted phenyl alkenylamines may be prepared in a similar manner to that illustrated in Preparation C using the appropriate starting alkanoic acid derivatives.

EXAMPLE 1

2-[N-(6-Phenylhexylamino)]-5-hydroxy-4-methylpyrimidine

[Formula I: R=H; R'=C$_6$H$_5$(CH$_2$)$_6$]

A mixture of 3.0 g (0.024 mole) of 5-acetyl-2-aminooxazole (Preparation A), 15 ml of 6-phenylhexylamine (Preparation B), and 3.3 ml of water was heated at 110° C. for 4.5 hours. The mixture was cooled to room temperature, 15 ml of isopropanol was added, and the mixture was allowed to stand at 5° C. for 17 hours. The resulting precipitate, which is 2-[N-(6-phenylhexylamino)]-5-acetyl-1H-imidazole, was collected and set aside. Concentration of the filtrate afforded an oil which was chromatographed over silica gel using 1:1 ethyl acetate/hexane as eluent. The less polar material was the desired product which was initially isolated as an oil but which solidified on standing. Recrystallization from 4:1 hexane/toluene afforded 811 mg (12%) of the title compound as a tan crystalline solid, mp 72°–74° C.

Analysis: CALC. C, 71.55; H, 8.12; N, 14.72. FOUND 71.55; 7.87; 14.66.

EXAMPLE 2

2-[N-(5-Phenylpentylamino)]-5-hydroxy-4-methylpyrimidine

[Formula I: R=H; R'=C$_6$H$_5$(CH$_2$)$_5$]

A mixture of 2.5 g (0.020 mole) of 5-acetyl-2-aminooxazole, 15 ml of 5-phenylpentylamine, 30 ml of water, and 20 ml of isopropanol, was heated at reflux for 24 hours. The mixture was cooled with an ice bath and the resulting precipitate, which was 2-[N-(5-phenylpentylamino)]-5-acetyl-1H-imidazole, was collected and set aside. The filtrate was concentrated and the oil residue was distilled under high vacuum to remove the excess amine. The dark residue was then chromatographed over silica gel using 9:1 ethyl acetate/hexane as eluent. The less polar material was the desired product which was isolated as an oil initially. Trituration of this oil with 1:1 toluene/cyclohexane gave 346 mg (6%) of the title compound as a white crystalline solid, mp 80°–82° C.

Analysis: CALC. C, 70.82; H, 7.99; N, 15.49. FOUND 70.59; 7.79; 15.49.

EXAMPLE 3

2-[N-(4-Phenylbutylamino)]-5-hydroxy-4-methylpyrimidine

[Formula I: R=H; R'=C$_6$H$_5$(CH$_2$)$_4$]

A mixture of 2.5 g (0.020 mole) of 5-acetyl-2-aminooxazole, 15 ml of 4-phenylbutylamine, 30 ml of water, and 20 ml of isopropyl alcohol, was heated at reflux for 22.5 hours. The mixture was cooled and the alcohol was removed under reduced pressure. The precipitate, which was a 2-[N-(4-phenylbutylamino)]-5-acetyl-1H-imidazole, was collected and set aside. The filtrate was concentrated and the residue was chromatographed over silica gel using 4:1 ethyl acetate/hexane as eluent. The less polar material was the desired product which was initially isolated as an oil, but which solidified when triturated with hexane to give 445 mg (9%) of the title compound as a white crystalline solid, mp 101°–104° C.

Analysis: CALC. C, 70.01; H, 7.44; N, 16.33. FOUND 69.75; 7.37; 16.14.

EXAMPLE 4

2-[N-(3-Phenylpropylamino)]-5-hydroxy-4-methylpyrimidine

[Formula I: R=H; R'=C$_6$H$_5$(CH$_2$)$_3$]

A mixture of 2.5 g (0.020 mole) of 5-acetyl-2-aminooxazole, 20 ml of 3-phenylpropylamine, 30 ml of water and 10 ml of isopropyl alcohol was heated at 130° (external) for 9 hours. The mixture was concentrated, and the residue distilled under reduced pressure to remove the excess amine. Trituration of the residue with acetonitrile afforded a precipitate, which was 2-N-(3-phenylpropylamino)]-5-acetyl-1H-imidazole, and which was collected and set aside. Concentration of the filtrate, left an oil which was chromatographed over silica gel using 4:1 ethyl acetate/hexane as eluent. The less polar material was the desired product, and it was isolated as a solid. Recrystallization from cyclohexane afforded 0.46 g (10%) of the title compound as a white solid, mp 101°–103° C.

Analysis: CALC. C, 69.11; H, 7.04; N, 17.27. FOUND 68.89; 6.72; 16.94.

EXAMPLE 5

2-[N-(3-(p-Chlorophenyl)propylamino)]-5-hydroxy-4-methylpyrimidine

Formula I: R=H; R'=pCl-C$_6$H$_4$(CH$_2$)$_3$]

A mixture of 2.5 g (0.02 mole) of 5-acetyl-2-aminooxazole, 10.5 g (0.062 mole) of 3-(p-chlorophenyl)propylamine, and 2.7 ml of water was heated at 110° C. (external) for 16 hours. The mixture was allowed to cool to room temperature and diluted with 15 ml of water. The resulting precipitate, which is 2-[N-(3-(p-chlorophenyl)propylamino)]-5-acetyl-1H-imidazole, was collected and set aside. Concentration of the filtrate afforded as oil which was chromatographed over silica gel using 1:1 ethyl acetate/hexane as eluent. The less polar material was the desired product which was isolated as a solid. Recrystallization from acetonitrile afforded 0.71 g (13%) of the title compound, mp 99°–100° C.

Analysis: CALC. C, 60.54; H, 5.81; N, 15.13. FOUND 60.17; 5.74; 14.85.

EXAMPLE 6

2-[N-(5-(p-Chlorophenyl)pentylamino)]-5-hydroxy-4-methylpyrimidine

[Formula I: R=H; R'=pCl-C$_6$H$_4$(CH$_2$)$_5$]

A mixture of 1.00 g (0.008 mole) of 5-acetyl-2-aminooxazole, 3.35 g (0.017 mole) of 5-(p-chlorophenyl)pentylamine, and 1.5 ml of water was heated at 110° C. (external) for 20 hours. The mixture was cooled, then diluted with 7 ml of isopropanol. The resulting precipitate, which is 2-[N-5-(p-chlorophenyl)pentylamino)]-5-acetyl-1H-imidazole, was collected and set aside. Concentration of the filtrate afforded an oil which was chromatographed over silica gel using 1:1 ethyl acetate/hexane as eluent. The less polar material was the desired product and was isolated as a solid. Recrystallization from 4:1 ethyl acetate/hexane gave 0.59 g (24%) of the title compound as a crystalline solid, mp 69°–71° C.

Analysis: CALC. C, 62.84; H, 6.59; N, 13.79. FOUND 63.16; 6.59; 13.79.

EXAMPLE 7

2-Amino-5-hydroxy-4-methylpyrimidine

Formula I: R=H; R'=H]

A mixture of 10 g (0.079 mole) of 5-acetyl-2-aminooxazole, and 200 ml of conc. ammonium hydroxide was placed in a 500 ml three-necked round-bottomed flask fitted with a condenser and gas inlet tube. The mixture was heated at reflux and ammonia gas was bubbled into the mixture for 30 hours. The mixture was concentrated and the solid residue was taken up into ethanol and chromatographed over silica gel using 9:1 chloroform/methanol as eluent. The less polar material was the desired product and was isolated as a solid. Recrystallization from acetonitrile afforded 2.3 g (22%) of a crystalline solid, mp 202.5°–204° C.

Analysis: CALC. C, 47.99; H, 5.64; N, 33.50. FOUND 48.15; 5.64; 33.26

EXAMPLE 8

2-(N-Hexylamino)-5-hydroxy-4-methylpyrimidine

[Formula I: R=H; R'=CH$_3$(CH$_2$)$_5$]

A mixture of 8.0 g (0.63 mole) of 5-acetyl-2-aminooxazole, 44 ml of hexylamine, and 11 ml of water was heated at 140° C. (external) for 1.5 hours. The mixture was cooled to room temperature and diluted with 53 ml of water. The resulting precipitate, which is 2-N-hexylamino-5-acetyl-1H-imidazole, was collected and set aside. Concentration of the filtration left a dark oil which was chromatographed over silica gel using 9:1 ethyl acetate/hexane as eluent. The less polar material was the desired product which amounted to 2.02 g (20%) of a tan crystalline solid, mp 90°–91° C.

Analysis: CALC. C, 63.13; H, 9.15; N, 20.08. FOUND 63.02; 9.06; 20.09.

EXAMPLE 9

2-(N-Octylamino)-5-hydroxy-4-methylpyrimidine

[Formula I: R=H; R'=CH$_3$(CH$_2$)$_7$]

A mixture of 3.2 g (0.025 mole) of 5-acetyl-2-aminooxazole, 20 ml of octylamine, 40 ml of water, and 35 ml of isopropanol was heated at 110° C. (external) for 22 hours. The mixture was cooled and the resulting precipitate, which is 2-N-octylamino-5-acetyl-1H-imidazole was collected and set aside. Concentration of the filtrate left a dark oil which was chromatographed over silica gel using 4:1 ethyl acetate/hexane as eluent. The less polar material was the desired product which amounted to 302 mg of analytically pure white solid, mp 84.5°–87° C.

Analysis: CALC. C, 65.78; H, 9.77; N, 17.70. FOUND 65.39; 9.65; 17.65.

EXAMPLE 10

2-[N-(6-p-chlorophenyl)hexylamino]-5-hydroxy-4-methylpyrimidine

[Formula I: R=H; R'=pClC$_6$H$_4$(CH$_2$)$_6$]

A mixture of 2.5 g (0.020 mole) of 5-acetylaminooxazole, 10.4 g (0.049 mole) of 6-(p-chlorophenyl)hexylamine, and 3.5 ml of water was heated at 110° C. (external) for 20 hours. The mixture was concentrated to remove the water, and then chromatographed over silica gel using 1:1 ethyl acetate/hexane as eluent. The less polar material was the desired product and was isolated as a solid. Recrystallization from 4:1 ethyl acetate/hexane afforded 0.65 g (11%) of the title compound, mp 69°–72° C.

Analysis: CALC. C, 63.84; H, 6.93; N, 13.14. FOUND 64.06; 6.90; 12.87.

EXAMPLE 11

2-(4-Benzyl-N-piperidino)-5-hydroxy-4-methlpyrimidine

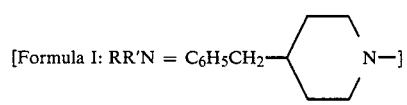
[Formula I: RR'N = C$_6$H$_5$CH$_2$—⟨N—⟩]

A mixture of 3.5 G (0.030 mole) of 5-acetyl-2-aminooxazole, 20 ml of 4-benzylpiperidine, and 5.2 ml of water was heated at reflux for 20 hours. The mixture was cooled to room temperature and diluted with 30 ml of water. The organic layer was separated and chromatographed over silica gel using 1:1 ethyl acetate/hexane as eluent. The less polar material was the desired product and was isolated as a solid. Recrystallization from toluene gave 0.77 g (10%) of the title product, mp 126°–128° C.

Analysis: CALC. C, 72.06; H, 7.47; N, 14.83. FOUND 72.23; 7.62; 14.82.

EXAMPLE 12

2-[4-(3-Phenylpropyl)-N-piperidino]-5-hydroxy-4-methylpyrimidine hydrochloride

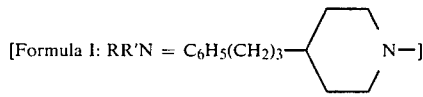
[Formula I: RR'N = C$_6$H$_5$(CH$_2$)$_3$—⟨N—⟩]

A mixture of 3.5 g (0.030 mole) of 5-acetyl-2-aminooxazole, 20 ml of 4-(3-phenylpropyl)piperidine, and 5.2 ml of water was heated at reflux for 20 hours. The mixture was cooled to room temperature and diluted with 30 ml of water. The organic layer was separated and chromatographed over silica gel using 1:1 ethyl acetate/hexane as eluent. The less polar material was the desired product and was isolated as an oil. This was converted to its hydrochloride by dissolving in 30 ml of ethanol, saturating this solution with hydrochloric acid gas, concentration of this hydrochloride solution to 5 ml and trituration with ether. In this way, 2.9 g (30%) of the hydrochloride salt of the title compound was isolated as an off-white solid, mp 149°–151° C.

Analysis: CALC. C, 65.60; H, 7.53, N, 12.08. FOUND 65.41; 7.50; 11.85.

EXAMPLE 13

2-N,N-Dimethylamino-5-hydroxy-4-methylpyrimidine

[Formula I: R=CH$_3$; R'=CH$_3$]

A mixture of 12 g (0.095 mole) of 5-acetyl-2-aminooxazole, and 350 ml of 40% dimethylamine in water was stirred at room temperature for 7 hours. The mixture was concentrated and the residue chromatographed over silica gel using 4:1 ethyl acetate/hexane as eluent. The less polar material was the desired product and was isolated as a solid. Recrystallization from cyclohexane afforded 6.4 g (44%) of the title compound as a white crystalline solid, mp 114°–116° C.

Analysis: CALC. C, 54.89; H, 7.24; N, 27.43. FOUND 54.91; 7.20 27.27.

EXAMPLE 14

2-(N-n-Nonylamino)-5-hydroxy-4-methylpyrimidine

[Formula I: R=H; R'=CH$_3$(CH$_2$)$_8$]

A mixture of 2.5 g (0.020 mole) of 5-acetyl-2-aminooxazole, 15 ml of n-nonylamine, 30 ml of water, and 25 ml of isopropanol was heated at reflux for 20 hours. The mixture was cooled, then distilled under reduced pressure to remove the excess n-nonylamine. The residue was chromatographed over silica gel using 7:2 ethyl acetate/hexane as eluent. The less polar material was the desired product, which amounted to 0.55 g of a brown solid. Recrystallization with hexane afforded 0.36 g (7%) of the title compound as a crystalline solid, mp 78°–81° C.

Analysis: Calculated for C$_{14}$H$_{25}$N$_3$O: CALC. C, 66.89; H, 10.02; N, 16.72. FOUND: 66.50 9.63; 16.66.

EXAMPLE 15

2-(N-2-Octylamino)-5-hydroxy-4-methylpyrimidine hydrochloride

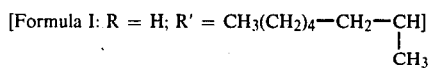

A mixture of 4.0 g (0.032 mole) of 5-acetyl-2-aminooxazole, 21.6 ml of 2-octylamine, and 5.6 ml of water was heated at reflux for 17.5 hours. The mixture was cooled, then distilled under reduced pressure to remove the excess 2-octylamine. The residue was chromatographed over silica gel using 9:1 ethyl acetate/hexane as eluent. The less polar material was the desired product which was isolated as a dark oil. This was taken up in methanol, saturated with hydrochloric acid gas, then concentrated. The residue was triturated with ether to give 1.56 g (13%) of the product as it hydrochloride salt, mp 118°–121° C.

Analysis: Calculated for $C_{13}H_{22}N_3O \cdot HCl \cdot \frac{1}{2}H_2O$: CALC. C, 55.20; H, 8.91; N, 14.86. FOUND: 55.71; 8.90; 14.86.

EXAMPLE 16

2-(N-n-Decylamino)-5-hydroxy-4-methylpyrimidine

[Formula I: R=H; R'=$CH_3(CH_2)_9$]

A mixture of 2.5 g (0.020 mole) of 5-acetyl-2-aminooxazole, 15 ml of n-decylamine, 30 ml of water, and 30 ml of isopropanol was heated at reflux for 20 hours. The mixture was cooled and the resulting precipitate, which is 2-n-decylamino-5-acetylimidazole, was set aside. The filtrate was concentrated and the oil residue was chromatographed over silica gel using 7:2 ethyl acetate/hexane as eluent. The less polar material was the desired product and this amounted to an 0.50 g of a gum. Crystallization with hexane gave 0.35 g (11%) of the title compound as a white solid, mp 82°–83° C.

Analysis: Calculated for $C_{15}H_{27}N_3O$: CALC: C, 67.88; H, 10.25; N, 15.83. FOUND: 67.49; 9.98; 15.77.

EXAMPLE 17

2-(N-Phenylamino)-5-hydroxy-4-methylpyrimidine

[Formula I: R=H; R'=$C_6H_5$]

A mixture of 2.5 g (0.020 mole) of 5-acetyl-2-aminooxazole, 15 ml of aniline, 30 ml of water, and 15 ml of isopropanol was heated at reflux for 91 hours. The mixture was cooled, and the isopropanol was removed under reduced pressure. The resulting yellow solid precipitate, which proved to be a mixture of 5-acetyl-2-aminooxazole and 2-N-phenylamino-5-acetylimidazole, was separated and set aside. The filtrate was concentrated under reduced pressure to remove the water and excess amine, and the residue chromatographed over silica gel using 2:1 hexane/ethyl aceate as eluent. The less polar material was the desired product and amounted to a brown solid. Recrystallization from acetonitrile afforded 0.18 g (4.5%) of the title compound, mp 164°–166° C.

Analysis: Calculated for $C_{11}H_{11}N_3O$: C, 65.66; H, 5.51; N, 20.88. Found: 65.21; 5.58; 20.51.

EXAMPLES 18–23

Following the general procedure described in the preceding Examples, a number of additional compounds according to the invention were prepared. Physical data and yields for these additional compounds are set out in the following Table I.

TABLE 1

Physical data for additional compounds of the formula:

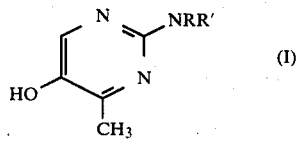

| Example No. | R | R' | M.P. °C. (recrystallization solvent) | Yield | Analytical Data | | | |
|---|---|---|---|---|---|---|---|---|
| 18 | H | $CH_2$=$CHCH_2$ | 122–125 (cyclohexane) | 13% | CALC. FOUND | C, 58.16; 57.97; | H, 6.71; 6.71; | N, 25.44 25.38 |
| 19 | H | $(CH_3)_2CHCH_2CH_2$ | 95–97 (cyclohexane) | 14% | CALC. FOUND | C, 61.51; 61.14; | H, 8.78; 8.44; | N, 21.52 21.39 |
| 20 | H | $CH_3CH_2\underset{\underset{CH_3}{\mid}}{CH}$ | 99–100.5 (pet. ether) | 23% | CALC. FOUND | C, 59.64; 59.35; | H, 8.34; 8.07 | N, 23.18 23.05 |
| 21 | H | $CH_3CH_2CH_2$ | 125–127 (toluene) | 15% | CALC. FOUND | C, 57.46; 57.40; | H, 7.84; 7.82; | N, 25.13 24.67 |
| 22 | H | Cyclopentyl | 122–124 (cyclohexane) | 12% | CALC. FOUND | C, 62.15; 61.89; | H, 7.82; 7.60; | N, 21.74 21.59 |
| 23 | H | 3-$CF_3C_6H_4(CH_2)_2$ (Hydrochloride salt) | 163–165 (methanol/diethyl ether) | 14% | CALC. AS .1HCl 1.5$H_2O$ FOUND | C, 46.48; 46.89; | H, 5.29; 4.70; | N, 11.62 11.85 |
| 24 | $CH_3$ | $CH_3(CH_2)_7$ (Hydrochloride salt) | 124–126.5 (ethanol/diethyl ether) | 10% | CALC. AS .1HCl FOUND | C, 58.42; 57.91; | H, 9.10; 9.15; | N, 14.60 14.35 |
| 25 | $CH_3$ | $CH_3(CH_2)_5$ (Hydrochloride salt) | 124–125 (ethanol/diethyl ether) | 7% | CALC. AS .1HCl FOUND | C, 55.48; 54.88 | H, 8.54; 8.37; | N, 16.18 15.75 |

I claim:

1. A method for treatment of gastro-intestinal disorders in a patient, which comprises administering to the patient a gastric anti-secretory effective amount of a substituted pyrimidine having the formula:

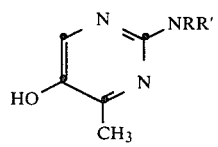 (I)

wherein R is hydrogen or $(C_1-C_{15})$alkyl and R' is hydrogen, $(C_1-C_{15})$alkyl, $(C_5-C_8)$cycloalkyl, $(C_3-C_{15})$alkenyl, phenyl, furyl, thienyl, $(C_7-C_{20})$aralkyl or substituted aralkyl wherein the substitutent is halo, $(C_1-C_3)$alkyl, $(C_1-C_3)$alkoxy or trifluoromethyl; or R and R' together with the nitrogen atom to which they are attached form a piperidyl group, a substituted piperidyl group wherein the substituent is $(C_1-C_{15})$alkyl or $(C_7-C_{20})$aralkyl, or a pyrrolidinyl group, or a pharmaceutically-acceptable acid addition salt thereof.

2. A method for the treatment of peptic ulcers and other gastrointestinal disorders in a patient, which comprises co-administering to the patient a pharmaceutically-effective amount of a compound according to claim 1 and an additional gastric anti-secretory agent.

3. A method according to claim 2, wherein the additional gastric anti-secretory agent is cimetidine, ranitidine, famotidine, etintidine, lamtidine or 2-guanidino-4-(2-methyl-4-imidazolyl)thiazole or a hydrohalide salt thereof.

* * * * *